United States Patent
Kimura et al.

(10) Patent No.: US 10,842,928 B2
(45) Date of Patent: Nov. 24, 2020

(54) ADAPTER FOR BLOOD DISPENSING

(71) Applicant: FUJIFILM Corporation, Tokyo (JP)

(72) Inventors: Toshihito Kimura, Kanagawa (JP); Toshiaki Kuniyasu, Kanagawa (JP); Hirotaka Watano, Kanagawa (JP); Akira Wakabayashi, Kanagawa (JP); Hiroshi Makino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 132 days.

(21) Appl. No.: 15/686,178

(22) Filed: Aug. 25, 2017

(65) Prior Publication Data

US 2018/0055990 A1 Mar. 1, 2018

(30) Foreign Application Priority Data

Aug. 30, 2016 (JP) .................................. 2016-167572

(51) Int. Cl.
*A61M 1/36* (2006.01)
*A61M 1/02* (2006.01)
(Continued)

(52) U.S. Cl.
CPC ........ *A61M 1/3687* (2013.01); *A61M 1/0218* (2014.02); *A61M 1/0259* (2013.01);
(Continued)

(58) Field of Classification Search
CPC .............. A61M 1/3687; A61M 1/0218; A61M 1/0259; B01F 1/00; B01L 3/0275
(Continued)

(56) References Cited

U.S. PATENT DOCUMENTS 5,538,735 A * 7/1996 Ahn ...................... A61K 9/0092
424/443
5,782,759 A * 7/1998 Chi .................... A61B 5/02007
600/369
(Continued)

FOREIGN PATENT DOCUMENTS

JP 2010501664 1/2010
JP 2013253989 12/2013
(Continued)

OTHER PUBLICATIONS

"Search Report of Europe Counterpart Application", dated Nov. 22, 2017, p. 1-p. 7, in which the listed references were cited.
(Continued)

*Primary Examiner* — Benjamin R Whatley
*Assistant Examiner* — Jacqueline Brazin
(74) *Attorney, Agent, or Firm* — JCIPRNET

(57) ABSTRACT

A medicine-holding body is disposed in a flow path of a nozzle portion of an adapter for blood dispensing. The medicine-holding body is formed of a plurality of fibers which is made of polyester and is bundled by aligning a longitudinal direction thereof in a flowing direction which is a direction in which blood flows. The medicine-holding body holds an anticoagulant for suppressing coagulation of blood, as a medicine to be mixed into blood. The surface area of the medicine-holding body is greater than or equal to 10 mm$^2$ and less than 600 mm$^2$. In a case where the surface area of the medicine-holding body is greater than or equal to 10 mm$^2$, the concentration of the anticoagulant becomes greater than or equal to a lower limit value of 10 U/mL even under most severe conditions such as a dispensing speed of 500 μL/second. In a case where the surface area of the medicine-holding body is less than 600 mm$^2$, it is possible (Continued)

to maintain the occurrence rate of hemolysis to be less than or equal to 10%.

5 Claims, 11 Drawing Sheets

(51) Int. Cl.
  *B01L 3/02* (2006.01)
  *B01L 3/00* (2006.01)
(52) U.S. Cl.
  CPC ............ *B01L 3/0275* (2013.01); *B01L 3/5021* (2013.01); *B01L 3/5635* (2013.01); *B01L 2200/026* (2013.01); *B01L 2200/16* (2013.01); *B01L 2300/0845* (2013.01)
(58) Field of Classification Search
  USPC .......................................................... 422/519
  See application file for complete search history.

(56) References Cited

U.S. PATENT DOCUMENTS

| | | | | |
|---|---|---|---|---|
| 2007/0232180 | A1* | 10/2007 | Polat | A61F 13/511 442/414 |
| 2007/0299384 | A1* | 12/2007 | Faul | A61B 17/11 604/8 |
| 2008/0197065 | A1* | 8/2008 | Wingo | B01D 39/1661 210/198.2 |
| 2008/0199357 | A1* | 8/2008 | Gellman | A61M 1/1698 422/48 |
| 2011/0092686 | A1 | 4/2011 | Motadel | |
| 2011/0107855 | A1 | 5/2011 | Motadel | |
| 2015/0209494 | A1* | 7/2015 | Muller | A61M 1/0272 210/321.89 |
| 2015/0265756 | A1* | 9/2015 | Yokomizo | A61M 1/0218 210/800 |
| 2015/0283318 | A1* | 10/2015 | Wang | A61B 18/20 210/638 |
| 2016/0100786 | A1* | 4/2016 | Nishio | B01L 3/0275 600/578 |
| 2017/0074758 | A1 | 3/2017 | Motadel | |
| 2018/0051312 | A1* | 2/2018 | Jaeger | B01L 3/0275 |

FOREIGN PATENT DOCUMENTS

| | | |
|---|---|---|
| JP | 2015-187592 | 10/2015 |
| WO | 2011077757 | 6/2011 |

OTHER PUBLICATIONS

"Office Action of European Counterpart Application," dated May 30, 2018, pp. 1-4.

"Office Action of Japan Counterpart Application", dated Aug. 6, 2019, with English translation thereof, p. 1-p. 6.

* cited by examiner

FIG. 6

| MATERIAL | CONTACT ANGLE (°) | REMARKS |
|---|---|---|
| POLYPROPYLENE | 91 | |
| POLYETHYLENE | 84 | |
| POLYESTER | 70 | |
| GLASS | 30 | THERE IS ELUTION INTO BLOOD |

45

HIGH WATER REPELLENCY
↕
HIGH HYDROPHILICITY

ADAPTER FOR BLOOD DISPENSING

CROSS-REFERENCE TO RELATED APPLICATION

This application claims priority under 35 USC 119 from Japanese Patent Application No. 2016-167572, filed 30 Aug. 2016, the disclosure of which is incorporated by reference herein.

BACKGROUND OF THE INVENTION

1. Field of the Invention

The present invention relates to an adapter for blood dispensing.

2. Description of the Related Art

An adapter for blood dispensing is used in a case of dispensing blood in an injector such as a pipette or a syringe into a sample container such as a centrifugal container. The adapter for blood dispensing is formed in a tubular shape and includes a fitting portion and a nozzle portion. The fitting portion is fitted with a distal portion of the injector and receives blood from the injector. A flow path through which blood flows toward the sample container is provided in the nozzle portion which is inserted into the sample container.

An adapter for blood dispensing in which a medicine-holding body (denoted as a carrier in JP2015-187592A) which holds a medicine such as an anticoagulant in a flow path of a nozzle portion is disposed is disclosed in JP2015-187592A. A sheet formed of cotton or a non-woven fabric capable of adsorbing a medicine is exemplified as the medicine-holding body in JP2015-187592A.

In a case where an adapter for blood dispensing is used, hemolysis (destruction of red blood cells) in a case of passing through the adapter for blood dispensing often becomes a problem. In a case where hemolysis occurs, it is impossible to accurately measure blood components. For this reason, it is necessary to avoid hemolysis as much as possible.

However, in the sheet which is formed of cotton or a non-woven fabric capable of adsorbing a medicine and is exemplified in JP2015-187592A as a medicine-holding body, the area where blood collides with the sheet during dispensing becomes comparatively large, and as a result, the number of times that red blood cells collide is increased. Therefore, the possibility of occurrence of hemolysis increases.

SUMMARY OF THE INVENTION

An object of the present invention is to provide an adapter for blood dispensing in which hemolysis hardly occurs.

In order to solve the above-described problem, there is provided an adapter for blood dispensing of the present invention comprising: a fitting portion which is fitted with a distal portion of an injector and receives blood from the injector; a nozzle portion in which a flow path, through which the blood flows toward a sample container, is provided and which is inserted into the sample container; and a medicine-holding body which is disposed in the flow path, holds a medicine to be mixed into the blood, and is formed of a plurality of fibers bundled by aligning a longitudinal direction thereof in a flowing direction which is a direction in which the blood flows.

It is preferable that the fibers are resins and are made of a material of which a contact angle is smaller than 80°. More specifically, it is preferable that the fibers are made of polyester.

It is preferable that a surface area of the medicine-holding body is greater than or equal to 10 mm$^2$ and less than 600 mm$^2$.

It is preferable that the medicine is an anticoagulant for suppressing coagulation of the blood.

In the present invention, the medicine-holding body which is disposed in the flow path of the nozzle portion and holds a medicine to be mixed into blood is formed of a plurality of fibers bundled by aligning a longitudinal direction thereof in a flowing direction which is a direction in which blood flows. Since the plurality of fibers are bundled by aligning a longitudinal direction thereof in a flowing direction, the area where blood collides with the fibers during dispensing is remarkably reduced, and as a result, it is possible to reduce the number of times that red blood cells collide with the fibers. Accordingly, it is possible to provide an adapter for blood dispensing in which hemolysis hardly occurs.

BRIEF DESCRIPTION OF THE DRAWINGS

FIG. 6 is a table showing characteristics of candidate materials of fibers forming the medicine-holding body.

DESCRIPTION OF THE PREFERRED EMBODIMENTS

Figure 1:
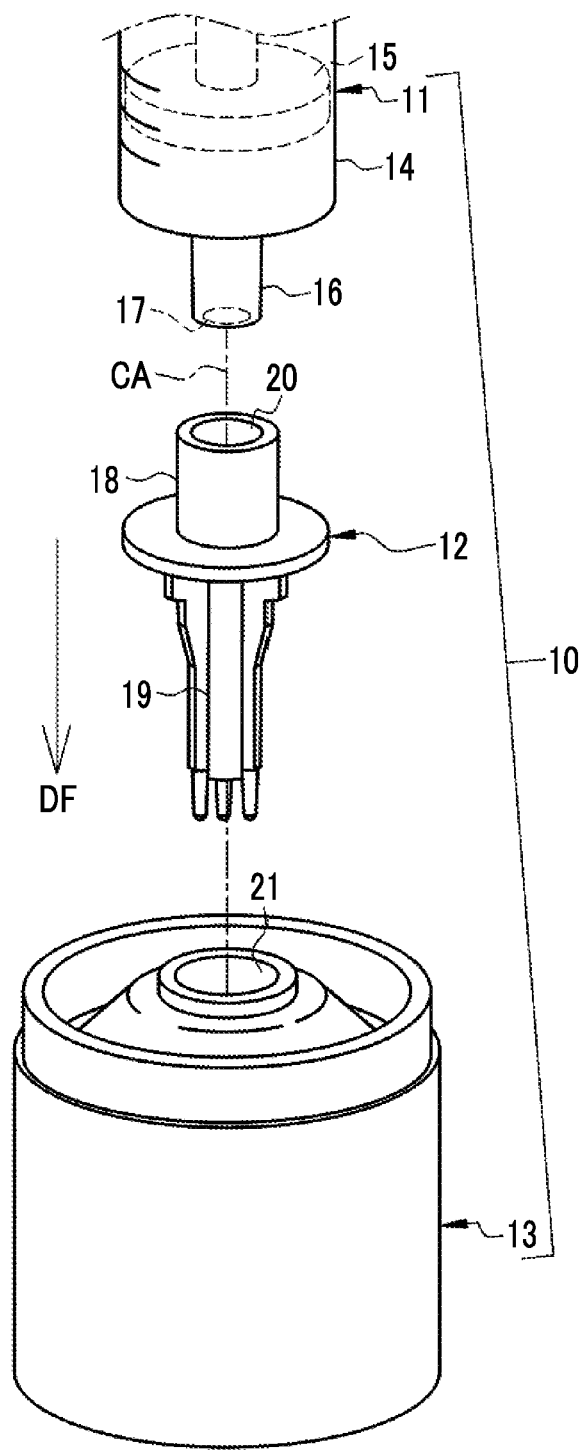
FIG. 1 is an exploded perspective view of a blood test kit.
Figure 2:
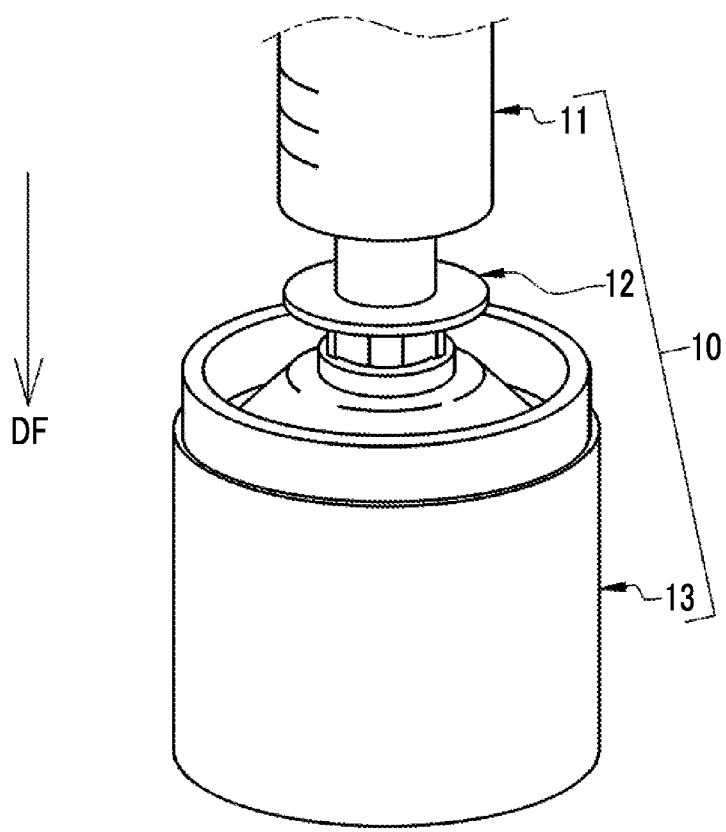
FIG. 2 is a perspective view showing a state where a syringe, an adapter for blood dispensing, and a centrifugal container are integrated.

A blood test kit 10 in FIGS. 1 and 2 is used for testing blood collected from a living body. The blood test kit 10 is configured of a syringe 11 corresponding to an injector, an adapter for blood dispensing 12, and a centrifugal container 13 corresponding to a sample container.

The syringe 11 has a cylindrical cylinder 14 and a plunger 15. A small-diameter distal portion 16 is provided in the cylinder 14. An opening 17 through which blood is drawn into the cylinder 14 and blood within the cylinder 14 is discharged is formed in the distal portion 16. The plunger 15 has a diameter substantially the same as the inner diameter of the cylinder 14 and is inserted into the cylinder 14 from a proximal end (not shown in the drawing) on a side opposite to the distal portion 16.

The adapter for blood dispensing 12 is made of a transparent resin, for example, polyethylene, polypropylene, and polystyrene and is formed into a tubular shape. The adapter for blood dispensing 12 has a fitting portion 18 and a nozzle portion 19. The fitting portion 18 has a fitting hole 20 having an inner diameter substantially the same as the outer diameter of the distal portion 16 of the syringe 11. The adapter for blood dispensing 12 is provided to a user in a state where the nozzle portion 19 is inserted into an injection port 21 of the centrifugal container 13. In a case of dispensing blood into the centrifugal container 13 from the syringe 11, the fitting hole 20 is fitted with the distal portion 16 of the syringe 11, and the adapter for blood dispensing enters a state shown in FIG. 2.

The centrifugal container 13 has a capacity of, for example, 600 µL to 1 mL. The centrifugal container 13 is a container for separating blood into, for example, a plasma component (or serum component) and a blood cell component consisting of red blood cells or white blood cells. The centrifugal container 13 is rotated by being put on a centrifugal separator (not shown in the drawing) after blood is dispensed. Since the plasma component (or serum component) and the blood cell component have different specific gravities, the plasma component (or serum component) and the blood cell component are centrifuged by the action of centrifugal force caused by this rotation.

The blood test kit 10 is a so-called disposal type blood test kit which is discarded after a single use and is used for each blood sample of a living body. The adapter for blood dispensing 12 and the centrifugal container 13 excluding the syringe 11 may be set as a disposal type.

An alternate long and short dash line shown by a reference numeral CA is a central axis of the syringe 11, the adapter for blood dispensing 12, and the centrifugal container 13. The syringe 11, the adapter for blood dispensing 12, and the centrifugal container 13 are integrated in a state where these central axes CA thereof are coincident with each other. An arrow shown by a reference numeral DF is a direction which is parallel to that of the central axis CA and is a flowing direction, that is, a direction in which blood flows from the syringe 11 to the centrifugal container 13 through the adapter for blood dispensing 12.

Figure 3:
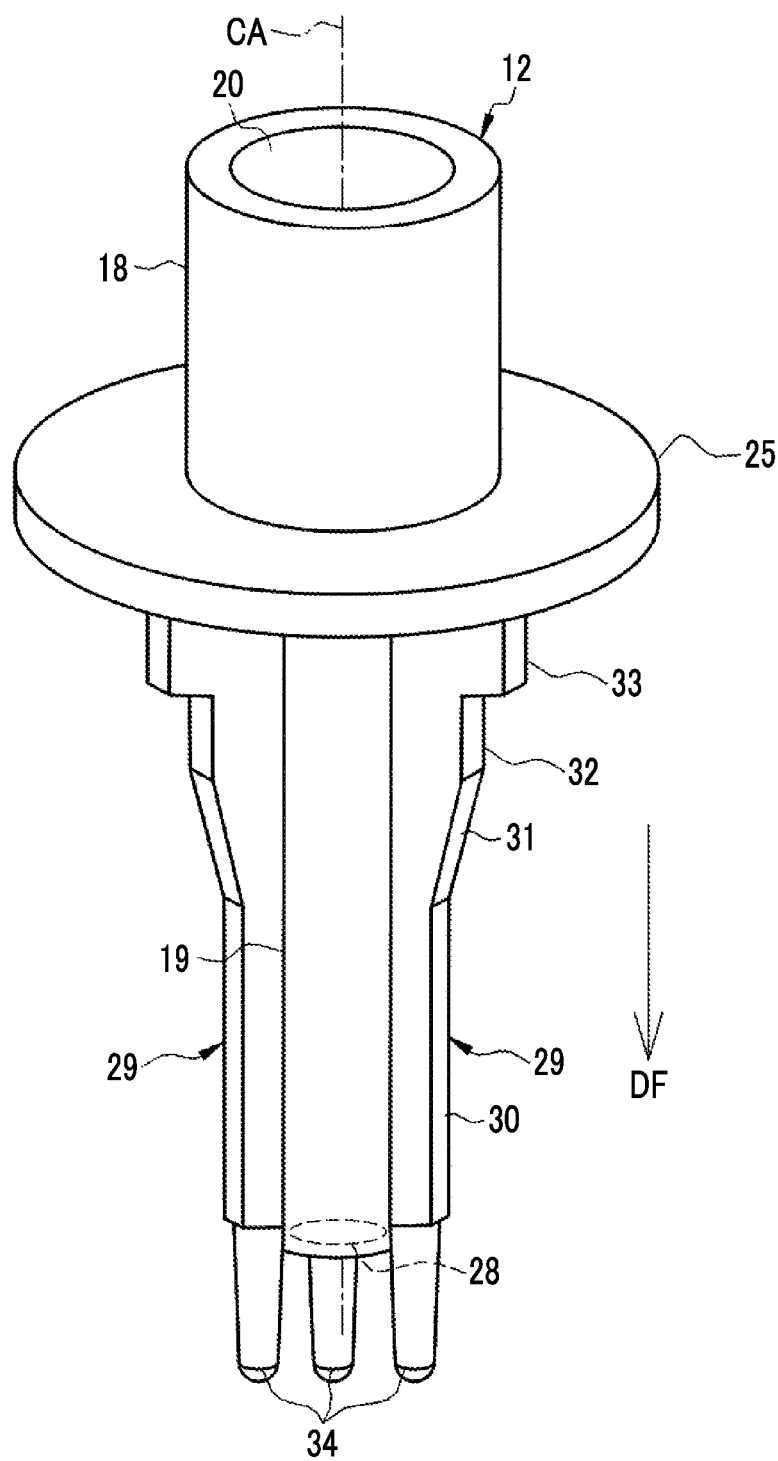
FIG. 3 is a perspective view of the adapter for blood dispensing.
Figure 4:
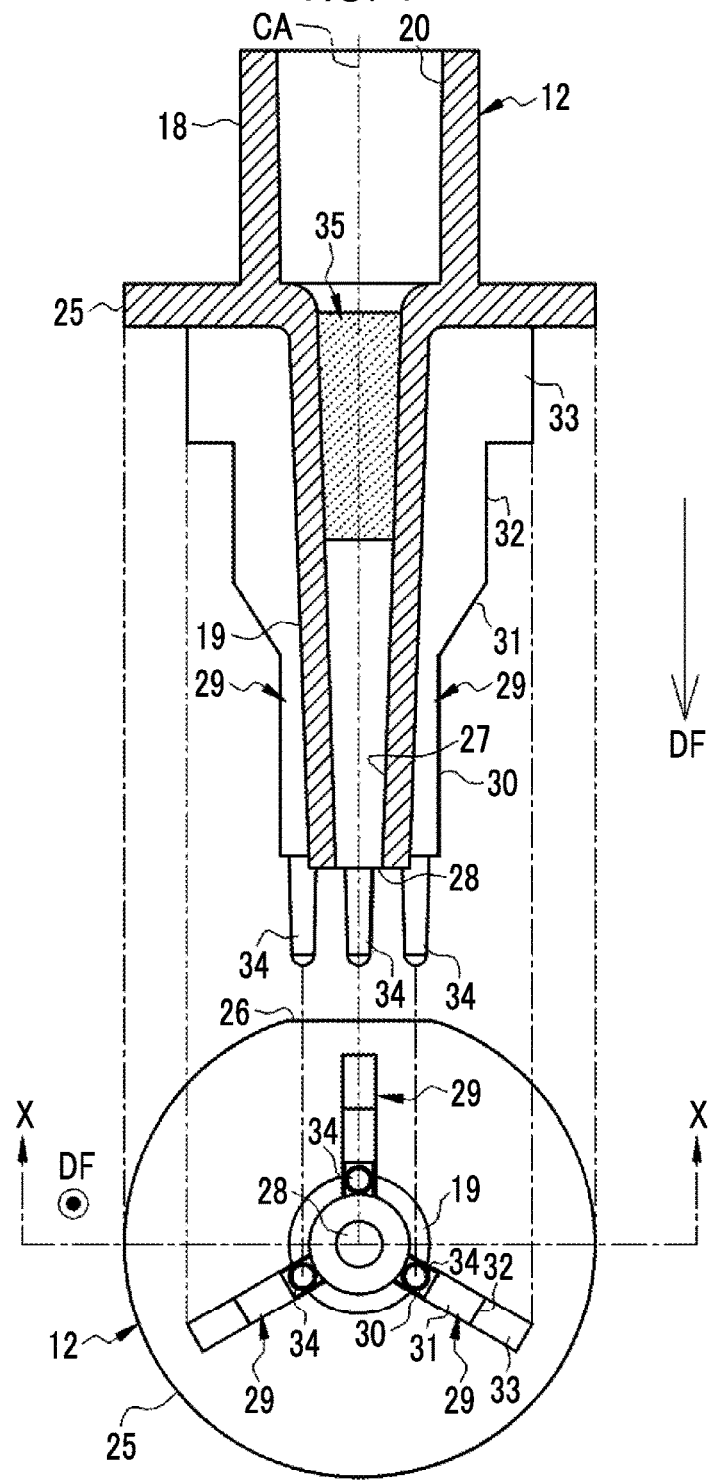
FIG. 4 shows a longitudinal sectional view (cut section of X-X) and a plan view of the adapter for blood dispensing.

In FIGS. 3 and 4 in which the adapter for blood dispensing 12 is shown in detail, a flange 25 is formed between the fitting portion 18 and the nozzle portion 19. The flange 25 is a disk protruding in a direction perpendicular to the central axis CA which is set as a center. The flange 25 functions as a gripping portion of the adapter for blood dispensing 12. A notch 26 for preventing rolling is provided in the flange 25.

The nozzle portion 19 has a substantially cylindrical shape in which the flow path 27 for blood is formed around the central axis CA. The flow path 27 communicates with the fitting hole 20 at an end on an upstream side (hereinafter, upstream end) in the flowing direction DF. In addition, a discharge port 28 of blood is formed at an end on a downstream side (hereinafter, downstream end) in the flowing direction DF of the flow path 27. That is, the fitting hole 20 and the discharge port 28 communicate with each other via the flow path 27. Blood from the syringe 11 is received by the fitting hole 20 and flows toward the discharge port 28 through the flow path 27.

The flow path 27 has a tapered shape of which the diameter is smaller than that of the fitting hole 20 at the upstream end and is gradually reduced toward the downstream end. The nozzle portion 19 also has the tapered shape of which the diameter is gradually reduced toward the downstream side from the upstream end, in accordance with the tapered shape of this flow path 27.

For example, the length of the adapter for blood dispensing 12 along the flowing direction DF is about 20 mm, the diameter of the fitting portion 18 is about 6 mm, the diameter of the flange 25 is about 12 mm, the diameter of the flow path 27 at the upstream end is about 2.2 mm, and the diameter of the downstream end is about 1.2 mm.

Three ribs 29 are formed on an outer peripheral surface of the nozzle portion 19 at equal intervals (every 120°). The ribs 29 are elongated thin plates which protrude in a direction orthogonal to the central axis CA and extend along the flowing direction DF. The ribs 29 are formed substantially over the entire length of the nozzle portion 19 from the flange 25 to the position in front of the discharge port 28.

Each rib 29 has a small piece portion 30, a tapered portion 31, a fitting portion 32, and a stopper portion 33 in order from the downstream end. The small piece portion 30 has a length from the position in front of the discharge port 28 to substantially a center of the nozzle portion 19. The protruding amount of the small piece portion 30 in a direction orthogonal to the central axis CA is smaller than the inner diameter of the injection port 21 of the centrifugal container 13. The tapered portion 31 is an inclined surface portion which connects the small piece portion 30 to the fitting portion 32. The protruding amount of the tapered portion increases from the small piece portion 30 toward the fitting portion 32.

The protruding amount of the fitting portion 32 is the same as or slightly larger than the inner diameter of the injection port 21. The stopper portion 33 protrudes from an edge of the fitting portion 32 at a right angle and the protruding amount thereof is larger than the inner diameter of the injection port 21.

In a case of inserting the nozzle portion 19 into the injection port 21, the small piece portion 30 of which the protruding amount is smaller than the inner diameter of the injection port 21 first passes through the injection port 21, and then, the tapered portion 31 passes through the injection port 21. At this time, the tapered portion 31 functions as a guide for allowing the fitting portion 32 to smoothly reach an edge of the injection port 21.

The fitting portion 32 has a protruding amount the same as or slightly larger than the inner diameter of the injection port 21. Therefore, the fitting portion comes into contact with the inner peripheral surface of the injection port 21 and is fitted with the injection port 21. Furthermore, in a case where the nozzle portion 19 is inserted into the injection port, the stopper portion 33 of which the protruding amount is larger than the inner diameter of the injection port 21 abuts on the edge of the injection port 21. Accordingly, insertion of the nozzle portion 19 into the injection port 21 is restricted.

As described above, the ribs 29 are disposed at intervals. For this reason, a ventilation path is secured between the outer peripheral surface of the nozzle portion 19 and the inner peripheral surface of the injection port 21 in a state where the nozzle portion 19 is inserted into the injection port 21. Gas-liquid exchange in a case of dispensing blood into the centrifugal container 13 is securely performed due to this ventilation path, and therefore, the dispensing is smoothly performed.

Three projection portions 34 are provided at downstream ends of the ribs 29 at equal intervals (every 120°) similarly to the ribs 29. The projection portions 34 are cylinders which are projected toward a downstream side in the flowing direction DF from the periphery of the discharge port 28. The projection portions 34 prevent remaining blood being pushed out from the discharge port 28 due to an effect of surface tension from adhering to the injection port 21 and the vicinity thereof, in a case of removing the nozzle portion 19 from the injection port 21 after the dispensing of blood.

The medicine-holding body 35 is disposed in the flow path 27. The medicine-holding body 35 is disposed from a portion of the flow path 27 of which the diameter is smaller than that of the fitting hole 20 at the upstream end to the position in front of the tapered portion 31 of each rib 29.

Figure 5:
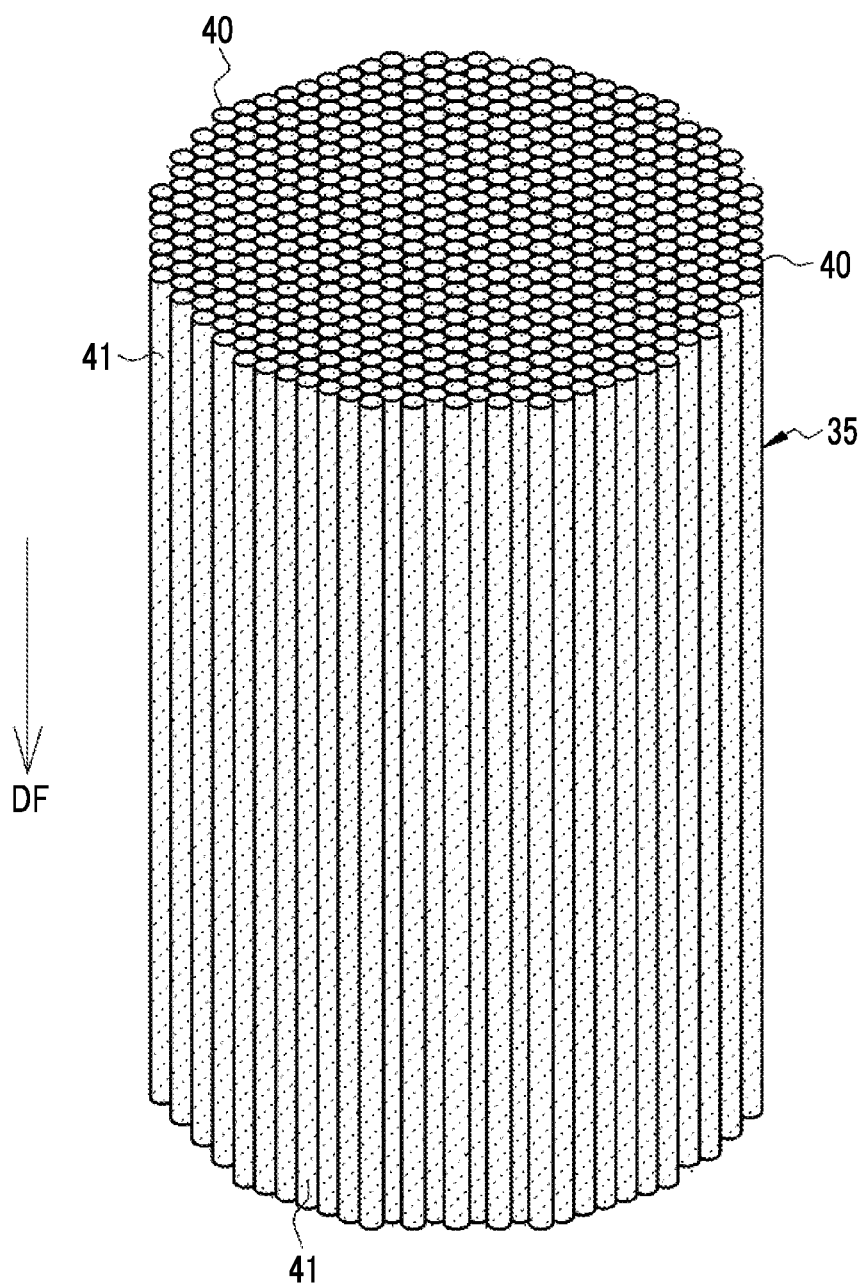
FIG. 5 is a perspective view of a medicine-holding body.

In FIG. 5, the medicine-holding body 35 is formed to have a cylindrical shape by bundling a plurality of elongated fibers 40 having a circular cross section. The fibers 40 are bundled by aligning a longitudinal direction thereof in the flowing direction DF. The fibers 40 have, for example, a diameter of 30 μm, a length of 5 mm, and a surface area of about 0.47 mm$^2$. The medicine-holding body 35 has, for example, a diameter of 2.2 mm.

The anticoagulant is adsorbed and held on the surface of each of the fibers 40 as a medicine as shown by hatching and a reference numeral 41. The anticoagulant 41 suppresses coagulation of blood. Examples of the anticoagulant 41 include ethylenediaminetetraacetic acid (EDTA), heparin sodium, heparin lithium, sodium citrate, trisodium citrate, fluoride, and potassium oxalate.

FIG. 6 is Table 45 showing characteristics of polypropylene, polyethylene, polyester, and glass which are candidate materials of the fibers 40. Among these materials, polypropylene has the largest contact angle. Then, the contact angle becomes smaller in order of polyethylene and polyester, and glass has the smallest contact angle. The larger the contact angle is, the higher the water repellency is. The smaller the contact angle is, the higher the hydrophilicity is. Therefore, among these, polypropylene has the highest water repellency. Then, the water repellency becomes lower in order of polyethylene and polyester. Glass has the highest hydrophilicity.

The contact angle refers to an angle formed between the surface of a liquid and the surface of a solid (in this case, a candidate material of the fibers 40) at a boundary line at which these three phases come into contact with each other, in a case where the surface of the solid comes into contact with a liquid (water) and gas (air). A liquid is added dropwise onto the surface of the solid parallel to the horizontal surface to be entered into a stationary state. Then, the state is photographed from a direction parallel to the horizontal surface to acquire an image. The acquired image is analyzed and the contact angle is measured using a contact angle meter which obtains the contact angle.

A material having comparatively high hydrophilicity, in specific, a material having a contact angle smaller than 80° is desired as the material for the fibers 40 constituting the medicine-holding body 35 in order to make adsorption of blood components hardly occur. From such viewpoint, glass is the most suitable material for the fibers 40 among the materials in Table 45. However, as described in remarks, calcium, chlorine, sodium and the like contained in glass are eluted into blood. For this reason, it is impossible to accurately measure the blood components. Accordingly, in the present invention, polyester which is a material, of which the hydrophilicity is next highest to glass and the contact angle is smaller than 80°, and is a resin in which there is no elution of contained components into blood, is employed as the material of the fibers 40.

In the material having a contact angle larger than or equal to 80° (in Table 45, polypropylene and polyethylene), a proportion of adsorbing blood components, in particular, proteins and red blood cells particularly increases. If the adsorption of blood components occurs, it is impossible to accurately measure the blood components. In a case where red blood cells are adsorbed, if the speed (hereinafter, referred to as dispensing speed) for dispensing blood into the centrifugal container 13 from the syringe 11 is comparatively high, hemolysis occurs. For this reason, it is preferable that the contact angle of the material of the fibers 40 is smaller than 80°. In addition, the material, such as glass in Table 45 or metal of which contained components are eluted into blood is not suitable as the material for the fibers 40. A resin of which contained components are not eluted into blood is preferable.

Here, the fibers 40 are made of polyester, but are not particularly limited as long as the material is a resin and the contact angle of the material is smaller than 80°. Examples thereof may include polyvinylidene chloride (75°), polyacrylonitrile (49°), NEOPRENE (registered trademark, 73°), nylon 6 (52°), N-methoxymethyl polyamide (62°), polymethyl acrylate (52°), polymethyl methacrylate (62°), polyvinyl chloride (68°), polyvinyl acetate (57°), VINYLON (registered trademark, 61°), cellulose diacetate (53°), cellulose triacetate (67°), a phenol resin (63°), and chlorinated rubber (68°).

The medicine-holding body 35 is constituted such that, in a case where a volume of 600 μL to 1 mL of blood with a hematocrit value of 30% to 55% is dispensed into the centrifugal container 13 from the syringe 11 over 1 second or longer, the concentration of the anticoagulant 41 in blood within the centrifugal container 13 (hereinafter, referred to as anticoagulant concentration) becomes 10 U/mL to 40 U/mL which is within a target range.

Specifically, 20 U of the anticoagulant 41 is held in the medicine-holding body 35. In this case, in a case where 500 μL of blood is dispensed into the centrifugal container 13 from the syringe 11, if all the anticoagulant 41 is dissolved in blood, the anticoagulant concentration becomes 40 U/mL which is an upper limit value of the target range. The actual amount of blood dispensed into the centrifugal container 13 is 600 μL to 1 mL which is the capacity of the centrifugal container 13. For this reason, if 20 U of the anticoagulant 41 is held in the medicine-holding body 35, the anticoagulant concentration in a case where all the anticoagulant 41 is dissolved in blood in a case where, for example, 600 μL of blood is dispensed becomes 20 U/600 μL≅33 U/mL, and therefore, does not exceed the upper limit value of 40 U/mL.

Figure 7:
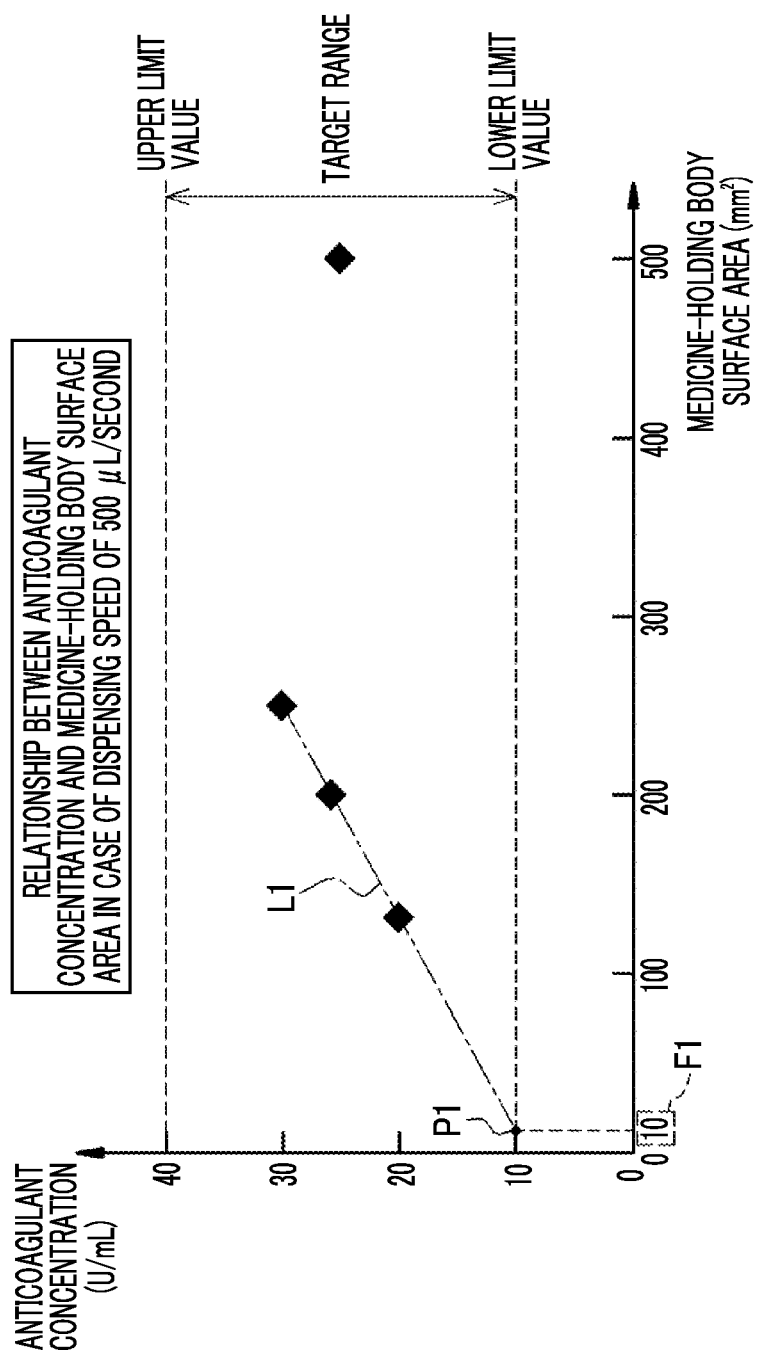
FIG. 7 is a graph showing a relationship between the anticoagulant concentration and the medicine-holding body surface area in a case of a dispensing speed of 500 µL/second.

FIG. 7 is a graph showing a relationship between the anticoagulant concentration and the surface area of the medicine-holding body 35 (hereinafter, referred to as medicine-holding body surface area) in a case of a dispensing speed of 500 μL/second. The dispensing speed of 500 μL/second is the highest dispensing speed that can be considered. If the dispensing speed is high, the amount of the anticoagulant 41 dissolved in blood is naturally decreased. For this reason, the dispensing speed 500 μL/second is the most severe condition for maintaining the anticoagulant concentration to be greater than or equal to 10 U/mL which is a lower limit value. In addition, the medicine-holding body surface area is a total surface area of a plurality of fibers 40 constituting the medicine-holding body 35 and is, specifically, a value obtained by multiplying the surface area of the fibers 40 by the number of fibers 40.

An approximate line L1 of three plots having a medicine-holding body surface area less than or equal to 300 mm$^2$ (excluding plots in the vicinity of a medicine-holding body surface area of 500 mm$^2$) is focused. The medicine-holding body surface area at a point P1 at which the approximate line L1 intersects with a line of the lower limit value of the anticoagulant concentration of 10 U/mL is 10 mm$^2$ as shown in a broken line frame F1. This shows that the anticoagulant concentration becomes greater than or equal to the lower limit value of 10 U/mL even under the most severe condition such as a dispensing speed of 500 μL/second if the medicine-holding body 35 has a surface area greater than or equal to 10 mm$^2$. Accordingly, the medicine-holding body 35 has a surface area greater than or equal to 10 mm$^2$ in order to make the anticoagulant concentration be greater than or equal to the lower limit value of 10 U/mL.

In a case where the anticoagulant concentration is less than the lower limit value of 10 U/mL, blood within the centrifugal container 13 coagulates. In contrast, in a case where the anticoagulant concentration exceeds the upper limit value of 40 U/mL, it exceeds an allowable amount of a film slide used for measuring blood components. In either case, it is impossible to accurately measure blood components.

The medicine-holding body 35 is formed such that the occurrence rate of hemolysis becomes less than or equal to 10%. Here, the occurrence rate refers to the probability that the effect Δ (=measurement result−measurement result in a case where there is no hemolysis) on Lactate Dehydrogenase (LDH) and Creatine PhosphoKinase (CPK) which are measurement items that are increased due to the occurrence of hemolysis, the effect being caused by hemolysis exceeds a prescribed range of ±20 U/L. The condition such as an occurrence rate of hemolysis being less than or equal to 10% is satisfied in a case where both of the occurrence rate of LDH and the occurrence rate of CPK are less than or equal to 10% and is a condition which the adapter for blood dispensing 12, as a product, need to at least satisfy.

Figure 8:
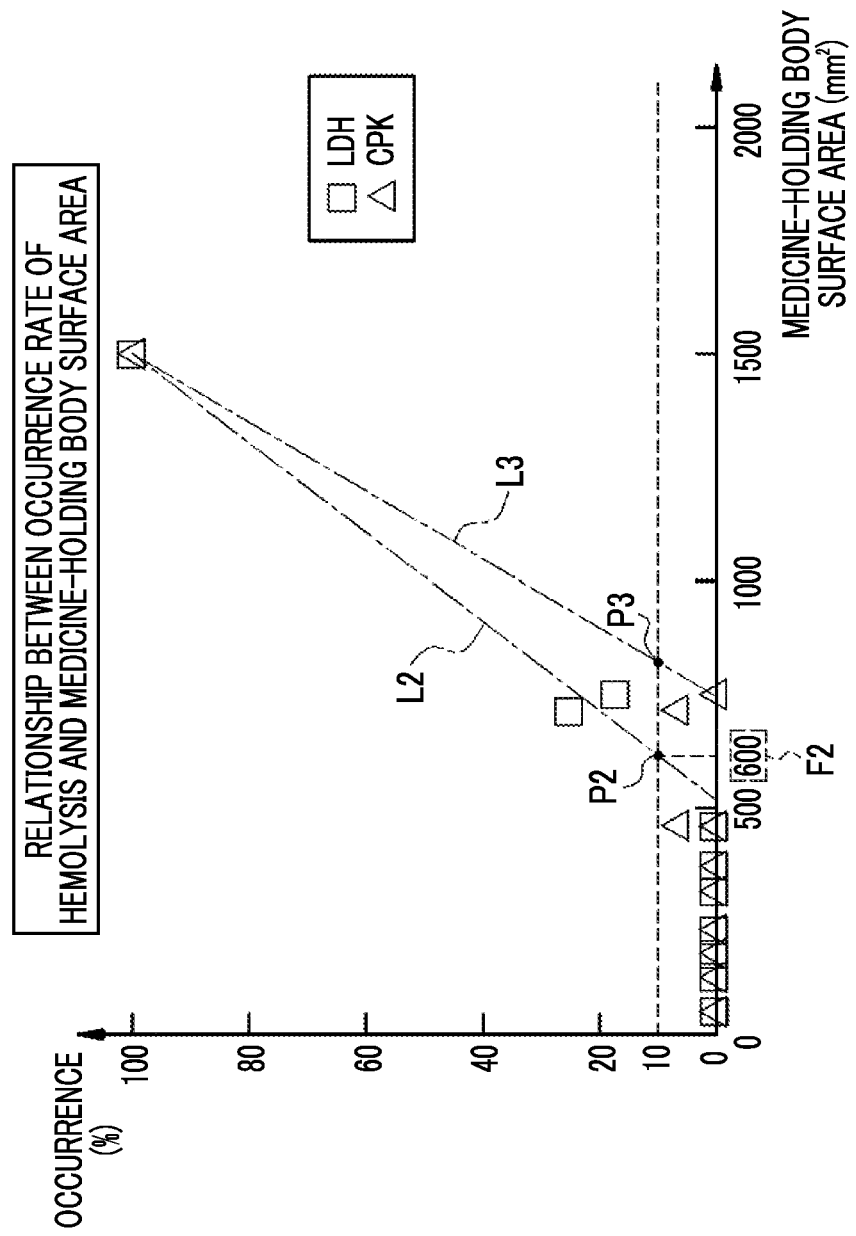
FIG. 8 is a graph showing a relationship between the occurrence rate of hemolysis and the medicine-holding body surface area.

FIG. 8 is a graph showing a relationship between the occurrence rate of hemolysis and the medicine-holding body surface area. A legend of a white blank rectangle and a legend of a white blank triangle respectively represent LDH and CPK. An approximate line L2 of a plot of LDH and an approximate line L3 of a plot of CPK are focused. First, the medicine-holding body surface area at a point P3 at which the approximate line L3 intersects with a line of the occurrence rate of 10% is about 750 mm$^2$. For this reason, if the medicine-holding body surface area is set to be about less than 750 mm$^2$, it is possible to at least suppress the occurrence rate of CPK to be less than or equal to 10%. However, in the case where the medicine-holding body surface area is about 750 mm$^2$, the occurrence rate of LDH exceeds 10%, and therefore, it is impossible to maintain the occurrence rate of hemolysis to be less than or equal to 10%.

In contrast, the medicine-holding body surface area at a point P2 at which the approximate line L2 intersects with the line of the occurrence rate of 10% is 600 mm$^2$ as shown by a broken line frame F2. In the case where the medicine-holding body surface area is 600 mm$^2$, both of the occurrence rate of LDH and the occurrence rate of CPK are less than or equal to 10%. For this reason, in the case where the medicine-holding body surface area is 600 mm$^2$, it can be seen that the occurrence rate of hemolysis is less than or equal to 10%. Accordingly, the medicine-holding body 35 has a surface area less than 600 mm$^2$ in order to maintain the occurrence rate of hemolysis to be less than or equal to 10%.

To summarize the description using FIGS. 7 and 8, the surface area of the medicine-holding body 35 is greater than or equal to 10 mm$^2$ and less than 600 mm$^2$. If the medicine-holding body surface area is greater than or equal to 10 mm$^2$, it is possible to maintain the anticoagulant concentration to be greater than or equal to 10 U/mL which is a lower limit value. In addition, if the medicine-holding body surface area is less than 600 mm$^2$, it is possible to maintain the occurrence rate of hemolysis to be less than or equal to 10%.

Figure 9:
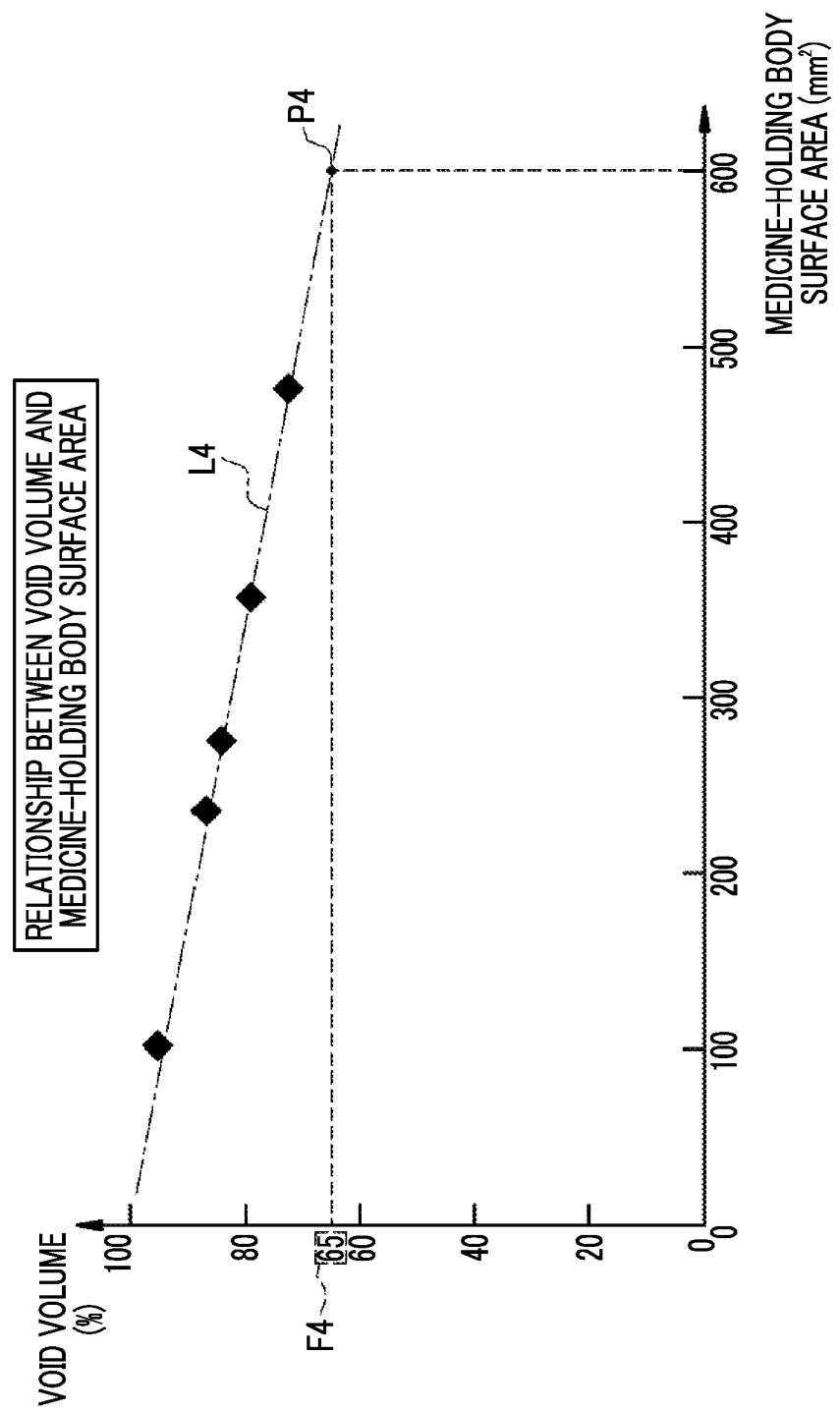
FIG. 9 is a graph showing a relationship between the void volume and the medicine-holding body surface area.

FIG. 9 is a graph showing a relationship between the void volume and the medicine-holding body surface area. Here, the void volume refers to a proportion (unit: %) of voids formed between the plurality of fibers 40 occupying the volume of the medicine-holding body 35 (radius of the medicine-holding body 35×radius×π×length) in a state where the medicine-holding body 35 is disposed in the flow path 27. The void volume at a point P4 at which an approximate line L4 with each plot intersects with a line of the medicine-holding body surface area of 600 mm$^2$ is 65% as shown by a broken line frame F4. That is, the medicine-holding body surface area of 600 mm$^2$ corresponds to a void volume of 65%. For this reason, the condition of maintaining the occurrence rate of hemolysis to be less than or equal to 10% which corresponds to the medicine-holding body surface area being less than 600 mm$^2$ which has been described using FIG. 8 can also be called a void volume being greater than 65%. The void volume in a case where the medicine-holding body surface area is 10 mm$^2$ is about 99.4%.

The volume of the medicine-holding body 35 is slightly compressed by disposing the medicine-holding body 35 in the flow path 27. For this reason, in order to make the void volume in a state where the medicine-holding body 35 is disposed in the flow path 27 be greater than 65%, it is necessary to make the void volume before the medicine-holding body is disposed in the flow path 27 be greater than 65% in a case of considering the fact that the volume of the medicine-holding body is slightly compressed. For example, in a case where the compression ratio of the volume of the medicine-holding body 35 due to the disposition of the medicine-holding body in the flow path 27 is 78%, if the void volume before the medicine-holding body is disposed in the flow path 27 is greater than 85%, 85 multiplied by 0.78 is 66.3. Therefore, the void volume in a state where the medicine-holding body 35 is disposed in the flow path 27 becomes greater than or equal to 65%.

Figure 10:
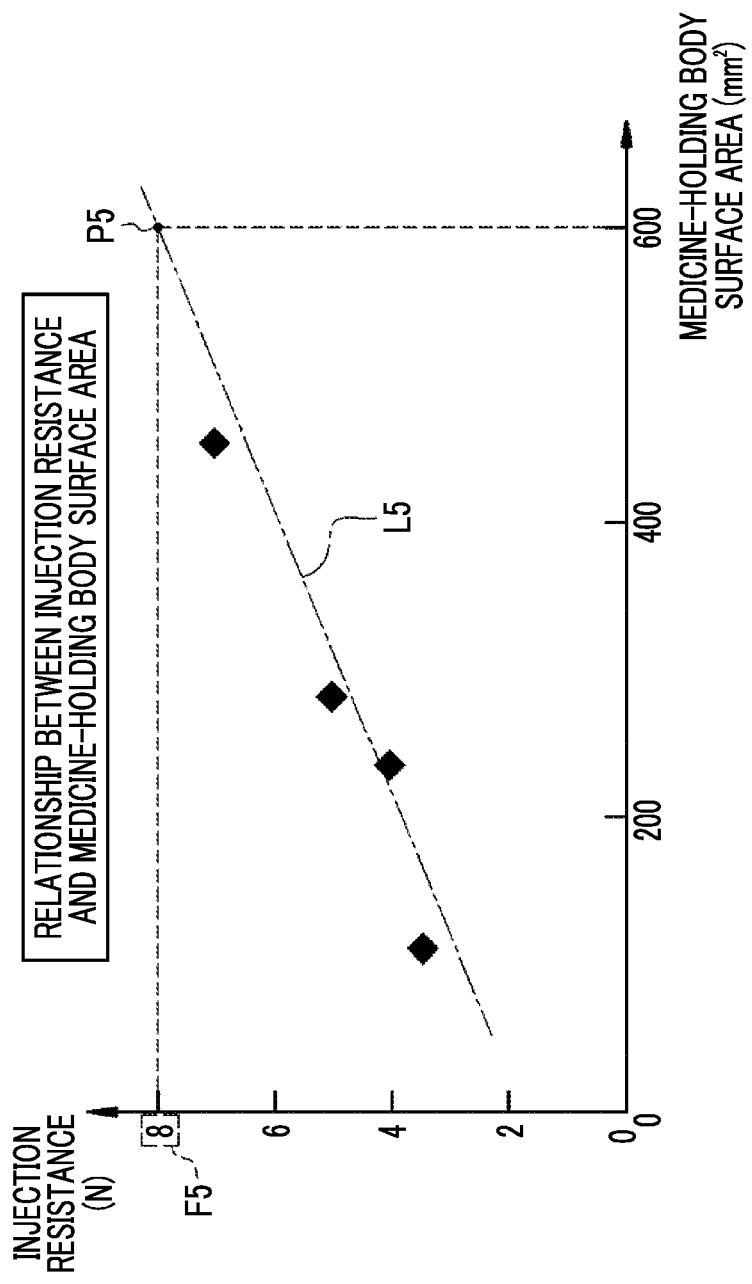
FIG. 10 is a graph showing a relationship between the injection resistance and the medicine-holding body surface area.

FIG. 10 is a graph showing a relationship between the injection resistance and the medicine-holding body surface area. Here, the injection resistance refers to a force (unit: N) required in a case of allowing blood to flow into the adapter for blood dispensing 12. The injection resistance at a point P5 at which an approximate line L5 of each plot intersects with a line of the medicine-holding body surface area of 600 mm$^2$ is 8 N as shown by a broken line frame F5. That is, the medicine-holding body surface area of 600 mm$^2$ corresponds to an injection resistance of 8 N. For this reason, the condition of maintaining the occurrence rate of hemolysis to be less than or equal to 10% which corresponds to the medicine-holding body surface area being less than 600 mm$^2$ which has been described using FIG. 8 can also be expressed as an injection resistance being less than 8 N. The injection resistance in a case of the medicine-holding body surface area being 10 mm$^2$ is about 1.5 N.

The medicine-holding body 35 may be commercially available on the market. For example, it is possible to use a polyester fiber rod manufactured by ASAHI FIBER INDUSTRY CO., LTD.

Next, an operation of the above-described configuration will be described. In a case of performing a blood test using the blood test kit 10, the adapter for blood dispensing 12 which is integrated with the centrifugal container 13 by inserting the nozzle portion 19 into the injection port 21 of the centrifugal container 13 is first prepared. Then, the adapter for blood dispensing 12 is attached to the syringe 11 by fitting the distal portion 16 of the syringe 11 in which blood is stored in the cylinder 14 with the fitting hole 20 of the adapter for blood dispensing 12 to make a state shown in FIG. 2.

Thereafter, the plunger 15 is pushed in the flowing direction DF. Accordingly, pressure is applied to the blood within the cylinder 14 and the blood is discharged from the opening 17. Blood discharged from the opening 17 is received by the fitting hole 20 of the adapter for blood dispensing 12 and passes through the medicine-holding body 35 disposed in the flow path 27. Accordingly, the anticoagulant 41 held in the medicine-holding body 35 is mixed into the blood.

The medicine-holding body 35 is formed of the plurality of fibers 40 bundled by aligning a longitudinal direction thereof in the flowing direction DF as shown in FIG. 5. In the case where the fibers 40 are bundled by aligning the longitudinal direction in the flowing direction DF, the area where blood collides with the fibers 40 during dispensing is remarkably reduced compared to a case where the fibers are bundled by aligning the longitudinal direction in a direction orthogonal to the flowing direction DF. As a result, it is possible to reduce the number of times that red blood cells collide with the fibers 40. Accordingly, hemolysis hardly occurs compared to the sheet which is formed of cotton or a non-woven fabric capable of adsorbing a medicine and is disclosed in JP2015-187592A.

The fibers 40 are made of polyester which is a material of which the contact angle is smaller than 80° as shown in FIG. 6. For this reason, the fibers have high hydrophilicity compared to the sheet which is formed of cotton or a non-woven fabric capable of adsorbing a medicine and is disclosed in JP2015-187592A, and therefore, adsorption of blood components hardly occurs. In addition, there is no elution of contained components into blood unlike glass. Accordingly, it is possible to maintain the accuracy of measurement of blood components at a high level.

Furthermore, the surface area of the medicine-holding body 35 is greater than or equal to 10 mm$^2$ and less than 600 mm$^2$ as shown in FIGS. 7 and 8. For this reason, it is possible to maintain the anticoagulant concentration to be greater than or equal to 10 U/mL which is a lower limit value and to maintain the occurrence rate of hemolysis to be less than or equal to 10%. Accordingly, it is possible to maintain the accuracy of measurement of blood components at a higher level.

A condition such as a medicine-holding body surface area being greater than or equal to 10 mm$^2$ is derived at the most severe dispensing speed of 500 μL/second. For this reason, even if the dispensing speed of blood is slightly changed by a user, it is possible to always maintain the anticoagulant concentration to be greater than or equal to 10 U/mL which is a lower limit value.

Blood mixed with the anticoagulant 41 is discharged from the discharge port 28 at the downstream end of the flow path 27 into the centrifugal container 13. After the blood is injected into the centrifugal container 13 in a predetermined amount, the adapter for blood dispensing 12 for each syringe 11 is removed from the centrifugal container 13.

After the removal of the adapter for blood dispensing 12, the centrifugal container 13 is put on a centrifugal separator, and the blood is centrifuged into plasma components (or serum components) and blood cell components. Then, the centrifuged components are collected on a film slide which is then put into a component analysis machine. The blood test is finally completed.

Figure 11:
FIG. 11 is a table showing the occurrence rate of hemolysis and the anticoagulant concentration in Comparative Examples and Example.

Table 50 in FIG. 11 shows the occurrence rate of hemolysis and the anticoagulant concentration (the lowest number of dispensing being 5 times) in a case where a volume of 600 μL of whole blood of a dog with a hematocrit value of 53% is dispensed 5 times over 3 seconds for each time (dispensing speed of 200 μL/second). Comparative Example 1 shows a case where the wall surface of the flow path 27 is coated with the anticoagulant 41 without using a medicine-holding body and Comparative Example 2 shows a case where the sheet formed of cotton or a non-woven fabric in JP2015-187592A is used as a medicine-holding body. Example shows a case where a medicine-holding body of the present invention formed of a plurality of fibers 40 bundled by arranging a longitudinal direction in the flowing direction DF is used. In all cases, heparin lithium is used as the anticoagulant 41. A solution obtained by dissolving 20 U of heparin lithium in a 1.0 wt % aqueous solution of polyvinyl alcohol was used for performing coating on the wall surface (Comparative Example 1) or for being immersed in the medicine-holding bodies (Comparative Example 2 and Example) and was dried.

In the case of Comparative Example 1, the length of the wall surface of the flow path 27 coated with the anticoagulant 41 in the flowing direction DF is 4.5 mm. In the case of Comparative Example 2, the sheet formed of cotton or a non-woven fabric has a length of 4.5 mm, a thickness of 0.43 mm, a density of 75 g/m$^2$, a fiber diameter of about 50 μm, and a medicine-holding body surface area of about 220 mm$^2$. More specifically, the sheet in Comparative Example 2 is obtained such that a product having a product name of GLASS FIBER DIAGNOSTIC PAD and a product model number of GFDX 203000 manufactured by Merck Millipore Corporation is suitably unraveled by cutting the product in a length of 4.5 mm. In the case of Example, the fibers 40 have a diameter of 30 μm, a length of 4.5 mm, and a medicine-holding body surface area of about 249 mm$^2$, and the number of fibers is 586.

According to Table 50, in Comparative Example 2, one dispensing out of the 5 times could not be performed and the effect Δ caused by hemolysis exceeded the prescribed range in 3 times of dispensing including the one time of dispensing which could not be performed. Therefore the occurrence rate is 60% which is high. In contrast, hemolysis did not occur in 5 times of dispensing in either of Comparative Example 1 and Example. In addition, in Comparative Example 1, the anticoagulant concentration is 2 U/mL which is much less than 10 U/mL of the lower limit value. In contrast, the anticoagulant concentration in Comparative Example 2 is 32 U/mL and the anticoagulant concentration in Example is 28 U/mL, which are within the target range of 10 U/mL to 40 U/mL. Accordingly, in Comparative Example 1, the anticoagulant concentration is not within the target range even though there is no occurrence of hemolysis. In addition, in Comparative Example 2, hemolysis occurs even though the anticoagulant concentration is within the target range. In contrast, in Example, it was confirmed that there was no occurrence of hemolysis and the anticoagulant concentration was within the target range.

A resin such as polyester has been exemplified as the material of the fibers 40. However, other materials except for resin may be used as long as there is no elution of the contained components into blood and the contact angle is smaller than 80°.

A coagulation accelerant for promoting coagulation of blood or a separating agent (a serum separating agent or a plasma separating agent) may be used as a medicine instead of the anticoagulant 41. Examples of the coagulation accelerant include silica, thrombin, and diatomaceous earth. An example of the separating agent includes polyester gel.

The injector is not limited to the syringe 11 and may be a pipette. In addition, the sample container is not limited to the centrifugal container 13. Blood may be allowed to stand after being dispensed. Furthermore, the wall surface of the flow path 27 may be coated with a medicine as well as the medicine-holding body 35.

The present invention is not limited to the above-described embodiment, and as a matter of course, various configurations can be adopted without departing from the gist of the present invention.

EXPLANATION OF REFERENCES

10: blood test kit
11: syringe
12: adapter for blood dispensing
13: centrifugal container
14: cylinder
15: plunger
16: distal portion
17: opening
18: fitting portion
19: nozzle portion
20: fitting hole
21: injection port
25: flange
26: notch
27: flow path
28: discharge port
29: rib
30: small piece portion
31: tapered portion
32: fitting portion
33: stopper portion
34: projection portion
35: medicine-holding body
40: fiber
41: anticoagulant
45, 50: table
CA: central axis
DF: flowing direction
L1 to L5: approximate line
P1 to P5: point
F1, F2, F4, F5: frame

What is claimed is:

1. An adapter connected to a centrifugal container for blood dispensing comprising:
    a fitting portion which is fitted with a distal portion of an injector and receives blood from the injector;
    a nozzle portion connected to the fitting portion, in which a flow path, through which the blood flows toward the centrifugal container, extending from a tip of the injector to the centrifugal container is provided, wherein a plurality of ribs are disposed on an outer peripheral surface of the nozzle portion and the nozzle portion has a tapered shape with a diameter gradually decreasing toward the centrifugal container and is inserted into the centrifugal container;
    a medicine-holding body which is disposed in the flow path, holds a medicine to be mixed into the blood, and is formed of a plurality of fibers bundled by aligning a longitudinal direction thereof in a flowing direction which is a direction in which the blood flows; and
    a plurality of projection portions equally spaced around the perimeter of the nozzle portion, wherein the plurality of projection portions are respectively projected from the ribs toward a downstream side in the flowing direction from the bottom end of the nozzle portion.

2. The adapter connected to the centrifugal container for blood dispensing according to claim 1,
    wherein the fibers are resins and are made of a material of which a contact angle is smaller than 80° when in contact with the blood.

3. The adapter connected to the centrifugal container for blood dispensing according to claim 2,
    wherein the fibers are made of polyester.

4. The adapter connected to the centrifugal container for blood dispensing according to claim 1,
    wherein a surface area of the medicine-holding body is greater than or equal to 10 mm$^2$ and less than 600 mm$^2$.

5. The adapter connected to the centrifugal container for blood dispensing according to claim 1,
    wherein the medicine is an anticoagulant for suppressing coagulation of the blood.

* * * * *